(12) United States Patent
Ohmure et al.

(10) Patent No.: US 8,729,896 B2
(45) Date of Patent: May 20, 2014

(54) MAGNETIC RESONANCE IMAGING APPARATUS AND MAGNETIC RESONANCE IMAGING METHOD

(75) Inventors: Takahiro Ohmure, Otawara (JP); Takao Kasugai, Otawara (JP); Kensuke Shinoda, Otawara (JP); Isao Tatebayashi, Utsunomiya (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 643 days.

(21) Appl. No.: 13/016,022

(22) Filed: Jan. 28, 2011

(65) Prior Publication Data
US 2011/0187365 A1    Aug. 4, 2011

(30) Foreign Application Priority Data

Jan. 29, 2010   (JP) .................................. 2010-019525
Jan. 14, 2011   (JP) .................................. 2011-006061

(51) Int. Cl.
*G01V 3/00*   (2006.01)

(52) U.S. Cl.
USPC .......................................... 324/309; 324/307

(58) Field of Classification Search
USPC .................................. 324/309, 307, 306, 314
See application file for complete search history.

(56) References Cited

U.S. PATENT DOCUMENTS 6,068,595 A   *   5/2000   Miyazaki et al. .............. 600/410
7,190,992 B2       3/2007   Tatebayashi et al.
7,940,044 B2  *   5/2011   Griswold et al. ............. 324/309

FOREIGN PATENT DOCUMENTS

| CN | 1432341 A | 7/2003 |
|---|---|---|
| JP | 3-207243 | 9/1991 |
| JP | 2009-148463 | 7/2009 |

OTHER PUBLICATIONS

Isao, T. et al., JP Application No. 2003-290172, (Oct. 14, 2003), Abstract.
Office Action dated May 15, 2013 in CN 201110030200.8.

* cited by examiner

*Primary Examiner* — Louis Arana
(74) *Attorney, Agent, or Firm* — Nixon & Vanderhye PC

(57) ABSTRACT

In one embodiment, a magnetic resonance imaging apparatus includes an input unit and a direction setting unit. The input unit receives a setting operation to set a plurality of image taking regions within a position determining image, from an operator of the apparatus. The direction setting unit sets phase encoding directions for the plurality of image taking regions to be in the same direction as one another, regardless of setting operations performed by the operator via the input unit.

17 Claims, 11 Drawing Sheets

FIG.9A

| IMAGE TAKING SITE | IMAGE TAKING CROSS SECTION | BODY POSITION | PHASE ENCODING DIRECTION |
|---|---|---|---|
| SPINE | AXIAL | SUPINE | FRONT-TO-BACK DIRECTION (DIRECTION 11) |
| | | PRONE | FRONT-TO-BACK DIRECTION (DIRECTION 12) |
| | | LYING ON HIS/HER SIDE (RIGHT ARM) | FRONT-TO-BACK DIRECTION (DIRECTION 13) |
| | | LYING ON HIS/HER SIDE (LEFT ARM) | FRONT-TO-BACK DIRECTION (DIRECTION 14) |
| | | ⋮ | ⋮ |
| SPINE | SAGITTAL | SUPINE | HEAD-TO-TOE DIRECTION (DIRECTION 21) |
| | | PRONE | HEAD-TO-TOE DIRECTION (DIRECTION 22) |
| | | LYING ON HIS/HER SIDE (RIGHT ARM) | HEAD-TO-TOE DIRECTION (DIRECTION 23) |
| | | LYING ON HIS/HER SIDE (LEFT ARM) | HEAD-TO-TOE DIRECTION (DIRECTION 24) |
| | | ⋮ | ⋮ |

FIG.9B

| SHAPE OF IMAGE TAKING SITE | PHASE ENCODING DIRECTION |
|---|---|
| RECTANGLE | SHORT SIDE |

FIG.10

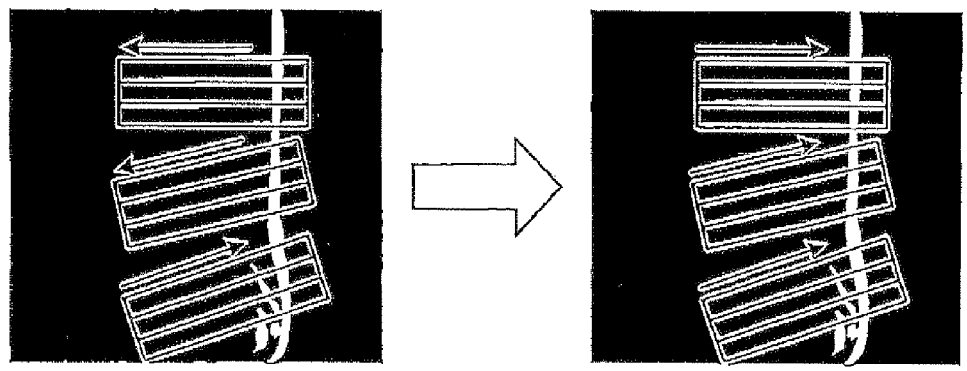

| IMAGE TAKING SITE | IMAGE TAKING CROSS SECTION | SEQUENCE | IMAGE TAKING METHOD | BODY POSITION | PHASE ENCODING DIRECTION |
|---|---|---|---|---|---|
| HEAD | AXIAL | EPI | DIFFUSION | SUPINE | PA DIRECTION (DIRECTION 3) |

| COIL | IMAGE TAKING CROSS SECTION | PHASE ENCODING DIRECTION |
|---|---|---|
| BREAST | AXIAL | LEFT-AND-RIGHT |

MAGNETIC RESONANCE IMAGING APPARATUS AND MAGNETIC RESONANCE IMAGING METHOD

CROSS-REFERENCE TO RELATED APPLICATION(S)

This application is based upon and claims the benefit of priority from Japanese Patent Application No 2010-019525, filed on Jan. 29, 2010, and Japanese Patent Application No. 2011-006061, filed on Jan. 14, 2011; the entire contents of all of which are incorporated herein by reference.

FIELD

Embodiments described herein relate generally to a magnetic resonance imaging apparatus and a magnetic resonance imaging method.

BACKGROUND

Magnetic Resonance Imaging apparatuses (hereinafter "MRI apparatuses") are apparatuses configured so as to obtain images of the inside of an examined subject with the use of a magnetic resonance phenomenon. Images (i.e., MRI images) that have been reconstructed by MRI apparatuses play an important role in various medical practices such as diagnosing and treating diseases and planning surgery.

When a diagnosis is made regarding the spine as having an intervertebral disc hernia, for example, MRI images are taken on a plurality of slice planes that are positioned parallel to one another along the spine. The plurality of slice planes that are positioned parallel to one another are collectively called a "slab". FIG. 17 is a drawing for explaining a slab setting process. To set a slab, as shown in FIG. 17 for example, an MRI image (i.e., a sagittal image) obtained by taking an image of the spine of an examined subject on a sagittal plane is displayed as a position determining image, which is used for determining the positions of one or more image taking regions.

Further, within the sagittal image, an operator of the apparatus sets, as shown in FIG. 17 for example, a slab that is made up of three slice planes that are positioned parallel to one another. After that, as shown in FIG. 17 for example, by setting three slabs from the upper part toward the lower part of the spine while varying the angles thereof, the operator determines the image taking regions for the MRI images to be used for making a diagnosis regarding the spine. In this situation, as a method for setting the slabs within the position determining image, a method has been known by which, for example, two points (i.e., a first point and a second point) are sequentially specified in the sagittal image by operating a mouse (for example, see JP-A 2003-290172 (KOKAI)).

According to this method, by using the mouse, the operator moves the cursor to the position indicated by a white dot in FIG. 17 and performs a clicking operation in that position, and subsequently, the operator moves the cursor to the position indicted by a black dot in FIG. 17 and performs a clicking operation in that position. As a result, while using the straight line defined by the two points as a center line, the MRI apparatus sets a slab, based on the center line and slicing conditions that have been set in advance (e.g., the number of slices, the thickness of the slices, and the length of the slices). According to this method, it is possible to change the slicing conditions after the slab has been set.

To reduce artifacts in MRI images, it is necessary, in particular, to set phase encoding directions appropriately For example, aliasing artifacts and flow artifacts are known as artifacts that are caused by the phase encoding direction setting process. FIG. 18 is a drawing for explaining a problem in the conventional technique.

According to the conventional technique described above, for example, each of the phase encoding directions is automatically set to be in the direction from the first point to the second point, as shown in FIG. 18. As a result, as shown in FIG. 18, in the case where the relative positional relationship between the first point and the second point is different for each of the slabs, the phase encoding direction is also different for each of the slabs. For this reason, the operator needs to perform an operation to change some of the phase encoding directions so that the phase encoding directions of all the slabs that have been set become the same as one another.

Further, not only when an image taking region is set by specifying two points, but also when a plurality of image taking regions are set by specifying rectangles within a position determining image while dragging a mouse, the conventional MRI apparatus sets the phase encoding directions along the directions in which the mouse was dragged. As a result, in the case where the moving direction corresponding to the dragging direction is different for each of the image taking regions, the phase encoding direction is also different for each of the image taking regions. For this reason, the operator needs to perform an operation to change some of the phase encoding directions so that the phase encoding directions for all the image taking regions that have been set become the same as one another.

As explained so far, according to the conventional technique described above, a burden is placed on the operator when the operator sets the phase encoding directions for the plurality of image taking regions that have been set within the position determining image.

BRIEF DESCRIPTION OF THE DRAWINGS

FIGS. 9A and 9B are drawings for explaining setting information data;

FIGS. 10 and 11 are drawings for explaining a direction setting unit according to the second embodiment;

DETAILED DESCRIPTION

In one embodiment, a magnetic resonance imaging apparatus includes an input unit and a direction setting unit. The input unit receives a setting operation to set a plurality of image taking regions within a position determining image, from an operator of the apparatus. The direction setting unit sets phase encoding directions for the plurality of image taking regions to be in the same direction as one another, regardless of setting operations performed by the operator via the input unit.

Exemplary embodiments of a magnetic resonance imaging apparatus will be explained in detail, with reference to the accompanying drawings. Hereinafter, a magnetic resonance imaging apparatus will be referred to as an "MRI apparatus".

Figure 1:
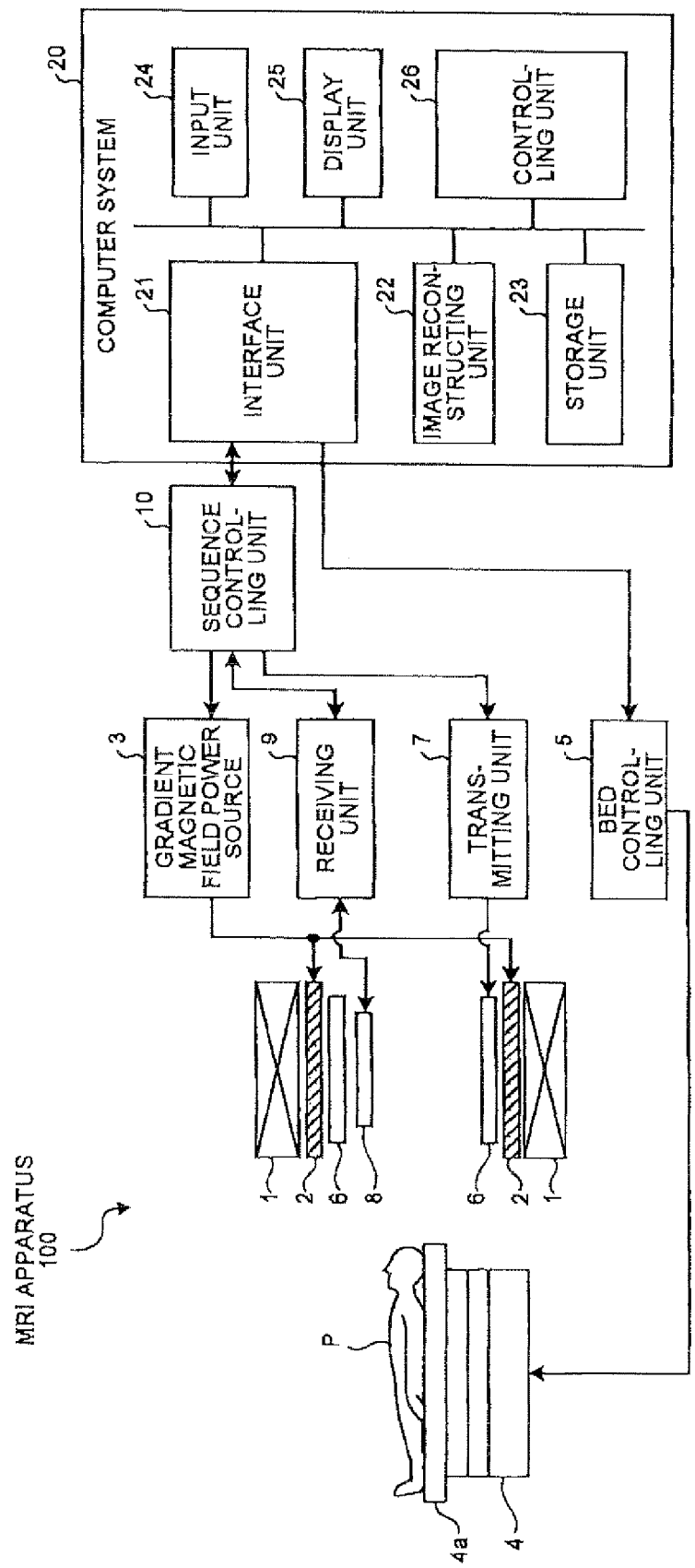
FIG. 1 is a drawing for explaining a configuration of an MRI apparatus according to a first embodiment.

First, a configuration of an MRI apparatus according to a first embodiment will be explained. FIG. 1 is a drawing for explaining a configuration of an MRI apparatus according to the first embodiment. As shown in FIG. 1, an MRI apparatus 100 according to the first embodiment includes a magnetostatic field magnet 1, a gradient magnetic field coil 2, a gradient magnetic field power source 3, a bed 4, a bed controlling unit 5, a transmission coil 6, a transmitting unit 7, a reception coil 8, a receiving unit 9, a sequence controlling unit 10, and a computer system 20.

The magnetostatic field magnet 1 is a magnet that is formed in the shape of a hollow circular cylinder and generates a uniform magnetostatic field in the space on the inside thereof. The magnetostatic field magnet 1 may be configured by using, for example, a permanent magnet, a superconductive magnet, or the like.

The gradient magnetic field coil 2 is a coil that is formed in the shape of a hollow circular cylinder and is disposed on the inside of the magnetostatic field magnet 1. The gradient magnetic field coil 2 is formed by combining three coils corresponding to X-, Y-, and Z-axes that are orthogonal to one another. These three coils individually receive a supply of electric current from the gradient magnetic field power source 3 (explained later) and generate gradient magnetic fields of which the magnetic field intensities change along the X-, Y-, and Z-axes. It is assumed that the Z-axis direction is the same as the direction of the magnetostatic field.

The gradient magnetic field power source 3 is a device that supplies the electric current to the gradient magnetic field coil 2.

The gradient magnetic fields on the X-, Y-, and Z-axes that are generated by the gradient magnetic field coil 2 correspond to, for example, a slice selecting gradient magnetic field, a phase encoding gradient magnetic field, and a read-out gradient magnetic field, respectively. The slice selecting gradient magnetic field is used for determining an image-taking cross section (i.e., a slice plane) in an arbitrary manner. The phase encoding gradient magnetic field is used far changing the phase of a magnetic resonance signal according to a spatial position. The read-out gradient magnetic field is used for changing the frequency of a magnetic resonance signal according to a spatial position.

The bed 4 includes a top plate 4a on which an examined subject P is placed. Under control of the bed controlling unit 5, while the examined subject P is placed thereon, the top plate 4a is inserted into the hollow (i.e., an image taking opening) of the gradient magnetic field coil 2. Normally, the bed 4 is provided so that the longitudinal direction thereof extends parallel to the central axis of the magnetostatic field magnet 1. The bed controlling unit 5 is a device that controls the bed 4 under control of a controlling unit 26 (explained later). The bed controlling unit 5 drives the bed 4 so that the top plate 4a moves in the longitudinal direction and in an up-and-down direction.

The transmission coil 6 is disposed on the inside of the gradient magnetic field coil 2 and generates a high-frequency magnetic field by receiving a supply of a high-frequency pulse from the transmitting unit 7.

The transmitting unit 7 transmits the high-frequency pulse corresponding to a Larmor frequency to the transmission coil 6. More specifically, the transmitting unit 7 includes, for example, an oscillating unit, a phase selecting unit, a frequency converting unit, an amplitude modulating unit, and a high-frequency electric-power amplifying unit. The oscillating unit generates a high-frequency signal having a resonance frequency that is unique to a target nucleus in the magnetostatic field. The phase selecting unit selects a phase of the high-frequency signal. The frequency converting unit converts the frequency of the high-frequency signal that has been output from the phase selecting unit. The amplitude modulating unit modulates the amplitude of the high-frequency signal that has been output from the frequency converting unit according to, for example, a sinc function. The high-frequency electric-power amplifying unit amplifies the high-frequency signal that has been output from the amplitude modulating unit.

The reception coil 8 is disposed on the inside of the gradient magnetic field coil 2 and receives a magnetic resonance signal emitted from the examined subject P due to an influence of the high-frequency magnetic field described above. Further, when having received the magnetic resonance signal, the reception coil 8 outputs the received magnetic resonance signal to the receiving unit 9.

The receiving unit 9 receives an input of the magnetic resonance signal that has been output from the reception coil 8 and generates magnetic resonance signal data. More specifically, the receiving unit 9 includes a selector, a multi-stage amplifier, a phase sensitive detector, and an analog/digital converter. The selector selectively receives an input of the magnetic resonance signal that has been output from the reception coil 8. The multi-stage amplifier amplifies the magnetic resonance signal that has been output from the selector. The phase sensitive detector detects the phase of the magnetic resonance signal that has been output from the multi-stage amplifier. The analog/digital converter generates the magnetic resonance signal data by digitally converting the signal that has been output from the phase sensitive detector.

Based on information regarding a pulse sequence (i.e., sequence information) that has been transmitted from the computer system 20, the sequence controlling unit 10 performs a scanning process on the examined subject P by driving the gradient magnetic field power source 3, the transmitting unit 7, and the receiving unit 9. Further, when the magnetic resonance signal data has been transmitted from the receiving unit 9 as a result of the scanning process performed on the examined subject P by driving the gradient magnetic field power source 3, the transmitting unit 7, and the receiving unit 9, the sequence controlling unit 10 transfers the magnetic resonance signal data to the computer system 20.

The "sequence information" is information that defines procedures for performing the scanning process along a time sequence and indicates, for example, the intensity of the electric power supply to be supplied by the gradient magnetic field power source 3 to the gradient magnetic field coil 2, the timing with which the electric power supply is to be supplied, the intensity of the high-frequency signal to be transmitted by the transmitting unit 7 to the transmission coil 6, the timing with which the high-frequency signal is to be transmitted, and the timing with which the magnetic resonance signal is to be detected by the receiving unit 9.

The computer system 20 exercises overall control of the MRI apparatus 100, collects data, and reconstructs images. The computer system 20 includes an interface unit 21, an image reconstructing unit 22, a storage unit 23, an input unit 24, a display unit 25, and the controlling unit 26.

The interface unit 21 controls inputs and outputs of various types of signals that are transmitted and received between the sequence controlling unit 10 and the computer system 20. For example, the interface unit 21 transmits the sequence information to the sequence controlling unit 10 and receives the magnetic resonance signal data from the sequence controlling unit 10. When having received the magnetic resonance signal data, the interface unit 21 stores the received magnetic resonance signal data into the storage unit 23.

The image reconstructing unit 22 is a processing unit that reconstructs image data (i.e., a magnetic resonance image) by performing post-processing, i.e., a reconstructing process such as a Fourier transform process, on the magnetic resonance signal data that has been stored in the storage unit 23.

The storage unit 23 stores therein, for example, the magnetic resonance signal data that has been received by the interface unit 21 and the image data that has been reconstructed by the image reconstructing unit 22, as well as various types of information that have been set by an operator of the apparatus.

The input unit 24 receives various types of operations and inputs of information from the operator. The input unit 24 includes a pointing device such as a mouse and/or a trackball, as well as a keyboard or the like. In collaboration with the display unit 25, the input unit 24 provides the operator of the MRI apparatus 100 with a user interface that is used by the MRI apparatus 100 to receive various types of operations from the operator.

Under control of the controlling unit 26 (explained later), the display unit 25 displays various types of information such as image data. The display unit 25 may be configured by using, for example, a display device such as a liquid crystal display monitor.

The controlling unit 26 includes a Central Processing Unit (CPU), a memory, and the like (not shown) and exercises overall control of the MRI apparatus 100. More specifically, the controlling unit 26 controls the scanning process by generating the sequence information based on image taking conditions that are input by the operator via the input unit 24 and transmitting the generated sequence information to the sequence controlling unit 10, and also, controls the image reconstructing process that is performed based on the magnetic resonance signal data sent from the sequence controlling unit 10 as a result of the scanning process.

As explained above, the MRI apparatus 100 according to the first embodiment is an apparatus that collects the magnetic resonance signal emitted from the inside of the examined subject P and reconstructs the magnetic resonance image. Further, the MRI apparatus 100 according to the first embodiment is an apparatus that is configured so as to be able to, in the case where a plurality of image taking regions have been set within a position determining image, make it easy to set the phase encoding directions for the plurality of image taking regions, under the control exercised by the controlling unit 26 described below.

Figure 2:
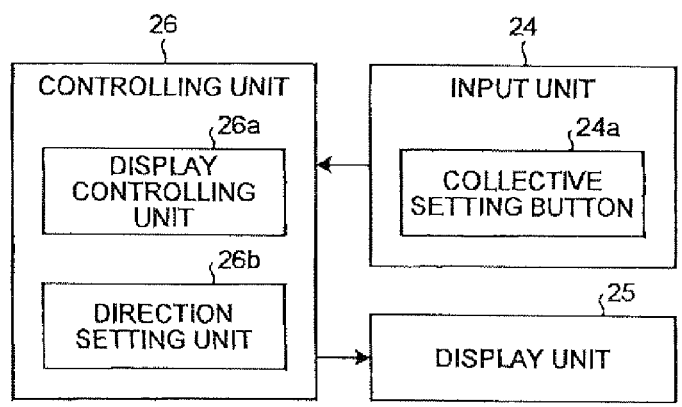
FIG. 2 is a drawing for explaining a configuration of a controlling unit according to the first embodiment.

In the following sections, processes performed by the controlling unit 26 according to the first embodiment will be explained with reference to FIGS. 2, 3A, 3B, 4A, 4B, and 4C. FIG. 2 is a drawing for explaining a configuration of the controlling unit according to the first embodiment. FIGS. 3A, 3B, 4A, 4B, and 4C are drawings for explaining a direction setting unit according to the first embodiment.

As shown in FIG. 2, the controlling unit 26 according to the first embodiment includes a display controlling unit 26a and a direction setting unit 26b. Further, the input unit 24 according to the first embodiment is provided with a collective setting button 24a.

The display controlling unit 26a exercises control so as to cause a monitor included in the display unit 25 to display image and the like. More specifically, the display controlling unit 26a exercises control so that the position determining image used for determining the position of an image taking region is displayed. For example, according to the first embodiment, when a diagnosis is made regarding the spine as having an intervertebral disc hernia, for example, an MRI image (i.e., a sagittal image) that is obtained by taking an image of the spine of the examined subject P on a sagittal plane is reconstructed by the image reconstructing unit 22 as a position determining image. Accordingly, the display controlling unit 26a reads the position determining image that has been stored in the storage unit 23 and causes the monitor included in the display unit 25 to display the read position determining image.

The input unit 24 receives a setting operation to set a plurality of image taking regions within the position determining image, from the operator. In other words, by operating the mouse included in the input unit 24, the operator refers to the position determining image and sequentially sets the plurality of image taking regions for the purpose of taking a plurality of MRI images on a plurality of slice planes that are positioned parallel to one another along the spine. More specifically, the operator sets the plurality of image taking regions by sequentially while changing the angles thereof, slabs each of which is made up of a plurality of slice planes that are positioned parallel to one another, under slicing conditions (e.g., the number of slices, the thickness of the slices, and the length of the slices) that have been set in advance. For example, by sequentially specifying two points (i.e., a first point and a second point) in the sagittal image while operating the mouse, the operator sets three slabs each of which is made up of three slice planes that are positioned parallel to one another.

The phase encoding directions for the image taking regions that have been set as a result of the mouse operation are set to be in such directions that extend along the moving directions of the mouse. Further, the display controlling unit 26a causes the phase encoding directions to be displayed, together with the plurality of image taking regions that have been set within the position determining image.

The direction setting unit 26b shown in FIG. 2 sets the phase encoding directions for the plurality of image taking regions to be in the same direction as one another, regardless of setting operations performed by the operator via the input unit 24. More specifically, in the case where a phase encoding direction setting request has been received from the operator via the input unit 24, the direction setting unit 26b sets the phase encoding directions for the plurality of image taking regions to be in the same direction as one another. Even more specifically, in the case where the operator has pressed the collective setting button 24a, the direction setting unit 26b sets the phase encoding directions for the plurality of image taking regions to be in the same direction as one another in a collective manner.

Figure 3A:
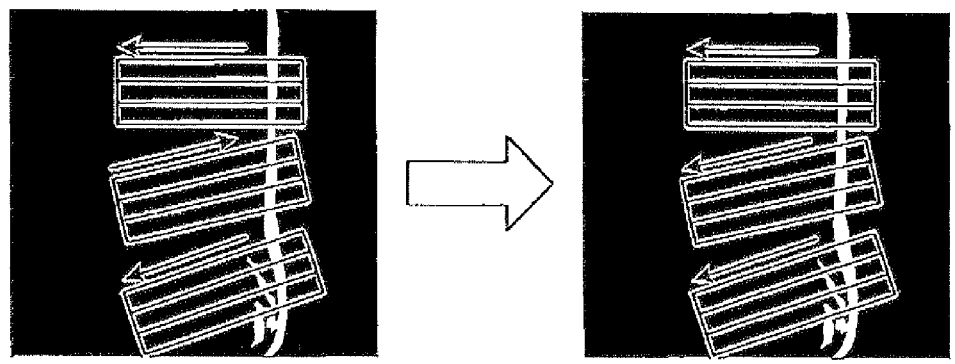
FIGS. 3A, 3B, 4A, 4B, and 4C are drawings for explaining a direction setting unit according to the first embodiment.

For example, as shown in the left portion of FIG. 3A, in the case where the phase encoding direction of the slab positioned in the middle among the three slabs is different from the phase encoding directions of the other slabs, the operator presses the collective setting button 24a. As a result, the direction setting unit 26b resets the phase encoding directions so that, as shown in the right portion of FIG. 3A, the phase encoding directions of all the slabs are in the same direction as one another (i.e., the back-to-front direction in the example shown in the drawing).

Further, as shown in the right portion of FIG. 3A, the display controlling unit 26a causes the display unit 25 to display an image in which the phase encoding directions of all the slabs are set to be in the back-to-front direction.

Figure 3B:
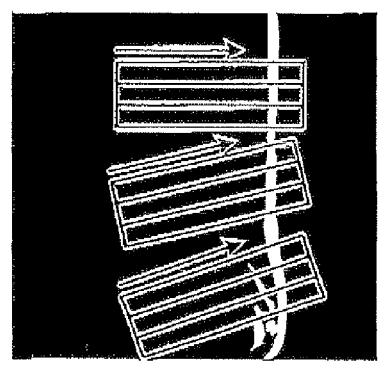

Further, when the operator refers to the image shown in the right portion of FIG. 3A and has pressed the collective setting button 24a again, the direction setting unit 26b resets the phase encoding directions so that, as shown in FIG. 3B, the phase encoding directions of all the slabs are in a front-to-back direction, which is the opposite of the back-to-front direction.

Figure 4A:
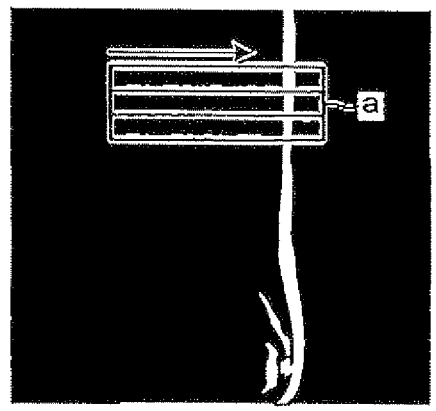

In the description above, the example has been explained in which, when the plurality of image taking regions that are made up of the plurality of slabs have been set in a collective manner, the phase encoding directions of the slabs are reset to be in the same direction as one another; however, the first embodiment may be applied to a situation in which, when a new slab has additionally been set, the phase encoding directions of the slabs are set to be in the same direction as one another. For example, let us discuss a situation in which, as shown in FIG. 4A, the operator has set a slab a, and subsequently, the operator additionally sets two slabs (i.e., a slab b and a slab c). In this situation, as shown in FIG. 4B for example, there is a possibility that the phase encoding direction of only the slab c may become different from the phase encoding directions of the other slabs, depending on which moving direction of the mouse is applied when the slabs were additionally set.

Figure 4B:
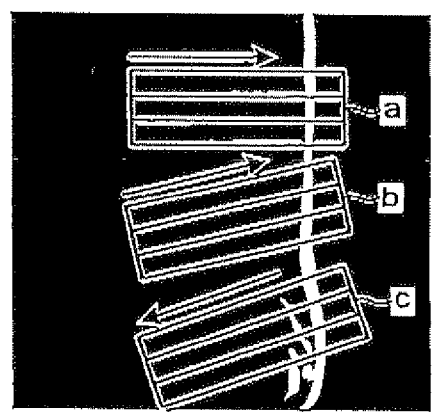
Figure 4C:
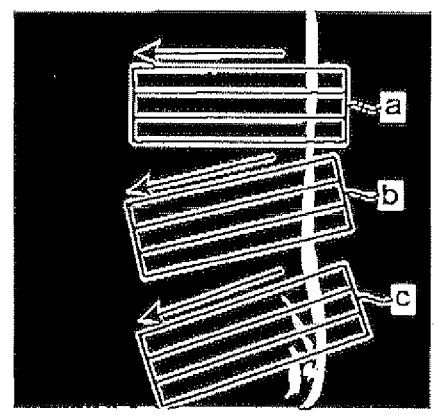

In that situation, when the operator refers to the image shown in FIG. 4B and has pressed the collective setting button 24a, the direction setting unit 26b sets the phase encoding directions of all the slabs to be, for example, in the back-to-front direction, as shown in FIG. 4C.

After the process by the direction setting unit 26b has been performed, the controlling unit 26 generates sequence information based on the phase encoding directions that have been set and transmits the generated sequence information to the sequence controlling unit 10 via the interface unit 21. Accordingly, the MRI apparatus 100 performs an MRI image taking process in the plurality of image taking regions.

The directions of the phase encoding directions that are set by the direction setting unit 26b may be decided by a majority (i.e., so as to adopt phase encoding directions that are the same as one another and form a majority), as shown in FIGS. 3A and 4C. Alternatively, the phase encoding directions may be set to a direction that is registered in advance. For example, an arrangement is acceptable in which the directions of the phase encoding directions that are set by the direction setting unit 26b are set, in a collective manner, to be in a direction from the right-hand side of the position determining image toward the left-hand side thereof.

Also, in the description above, the example has been explained as an exemplary embodiment in which, when the plurality of image taking regions have been set by using the slabs, the phase encoding directions for the image taking regions included in all the slabs are set to be in the same direction as one another; however, the first embodiment is not limited to this example. In other words, the first embodiment may be applied to a situation in which, when a plurality of image taking regions have been set by sequentially setting the image taking regions each of which is made up of one slice plane, the phase encoding directions for all the image taking regions are set to be in the same direction as one another.

Further, in the description above, the example has been explained as an exemplary embodiment in which the phase encoding directions for the plurality of image taking regions that have been set within the single position determining image (i.e., the sagittal image) are set to be in the same direction as one another within the position determining image; however, the first embodiment is not limited to this example. In other words, the first embodiment may be applied to a situation in which a plurality of position determining images (including, for example, one or more of any of the following: sagittal images, coronal images, axial images, and oblique cross-section images) are used. For example, let us discuss a situation in which the operator refers to a plurality of position determining images and has set a plurality of image taking regions, and also, by further referring to the position determining images in which the image taking regions and the phase encoding directions are rendered, the operator has selected one of the position determining images that is to be used for setting the phase encoding directions. In that situation, the direction setting unit 26b sets the phase encoding directions for the plurality of image taking regions to be in the same direction as one another, within the position determining image that has been selected by the operator.

Figure 5:
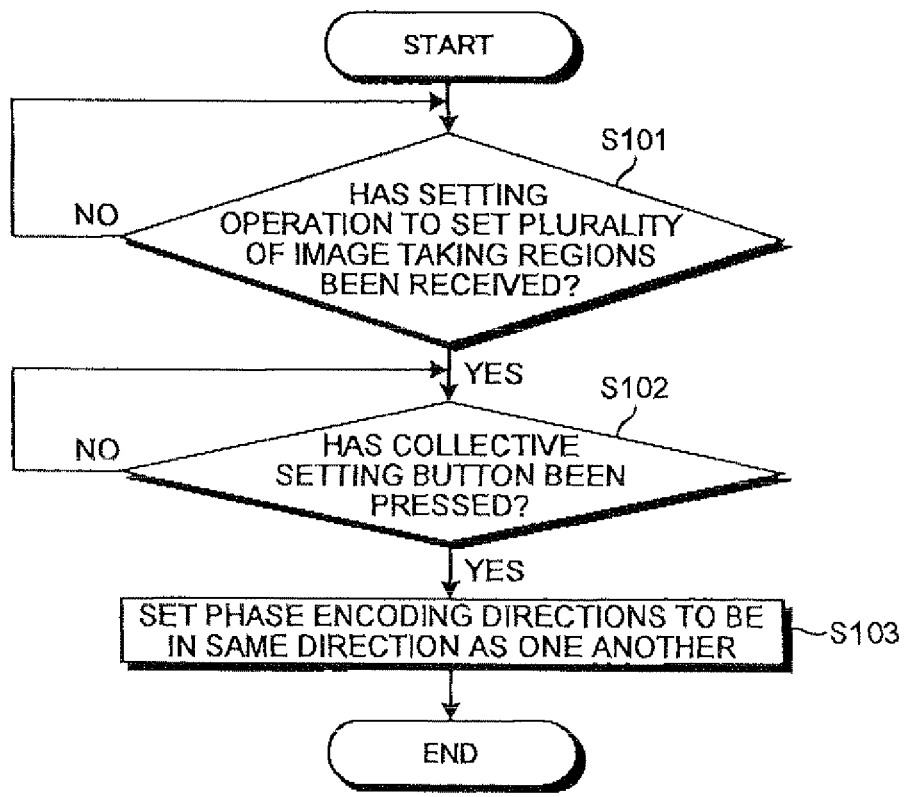
FIG. 5 is a flowchart for explaining a process performed by the MRI apparatus according to the first embodiment.

Next, a process performed by the MRI apparatus 100 according to the first embodiment will be explained, with reference to FIG. 5. FIG. 5 is a flowchart for explaining the process performed by the MRI apparatus according to the first embodiment.

As shown in FIG. 5, the MRI apparatus 100 according to the first embodiment judges whether the input unit 24 has received a setting operation to set a plurality of image taking regions within a position determining image, from the operator (step S101). In this situation, in the case where a setting operation to set a plurality of image taking regions has not been received (step S101: No), the MRI apparatus 100 goes into a stand-by state. On the contrary, in the case where a setting operation to set a plurality of image taking regions has been received (step S101: Yes), the MRI apparatus 100 judges whether the collective setting button 24a has been pressed by the operator (step S102).

In this situation, in the case where the collective setting button 24a has not been pressed by the operator (step S102: No), the MRI apparatus 100 goes into a stand-by state.

On the contrary, in the case where the collective setting button 24a has been pressed by the operator (step S102: Yes), the direction setting unit 26b sets the phase encoding directions for the plurality of image taking regions to be in the same direction as one another (step S103), and the process is ended.

As explained above, according to the first embodiment, the input unit 24 receives the setting operation to set the plurality of image taking regions within the position determining image, from the operator. The direction setting unit 26b sets the phase encoding directions for the plurality of image taking regions to be in the same direction as one another, regardless of the setting operations performed by the operator via the input unit 24. More specifically, in the case where the collective setting button 24a has been pressed by the operator, the direction setting unit 26b sets the phase encoding directions for the plurality of image taking regions to be in the same direction as one another.

With this arrangement, according to the first embodiment, even if the phase encoding direction is different for each of the image taking regions, it is possible to arrange the phase encoding directions to be in the same direction as one another in a collective manner by only pressing the collective setting button 24a. Thus, it is possible to make it easy to set the phase encoding directions for the plurality of image taking regions. In addition, according to the first embodiment, by pressing the collective setting button 24a at the discretion of the operator, it is possible to change all the phase encoding directions for the plurality of image taking regions in a collective manner. Consequently, it is possible to reduce artifacts in the MRI images that are caused by the phase encoding direction setting process.

Further, according to the first embodiment, the display controlling unit 26a causes the monitor included in the display unit 25 to display the phase encoding directions for the plurality of image taking regions that have been set by the direction setting unit 26b. As a result, the operator is able to easily judge whether the phase encoding directions that have been set need to be corrected. Consequently, it is possible to make it even easier to set the phase encoding directions for the plurality of image taking regions.

In the description of the first embodiment, the example has been explained in which the process by the direction setting unit 26b is performed in the case where the collective setting button 24a has been pressed; however, the first embodiment is not limited to this example. In other words, the first embodiment may be applied to a situation in which the phase encoding directions for the plurality of image taking regions are set to be in the same direction as one another, without receiving any phase encoding direction setting request from the operator. More specifically, another arrangement is acceptable in which the direction setting unit 26b judges the direction of each of the phase encoding directions that have been set for the plurality of image taking regions as a result of a setting operation performed by the operator via the input unit 24 so that, if there are one or more image taking regions for which a different phase encoding direction has been set, the direction setting unit 26b automatically sets all the phase encoding directions to be in the same direction as one another in a collective manner.

Figure 6:
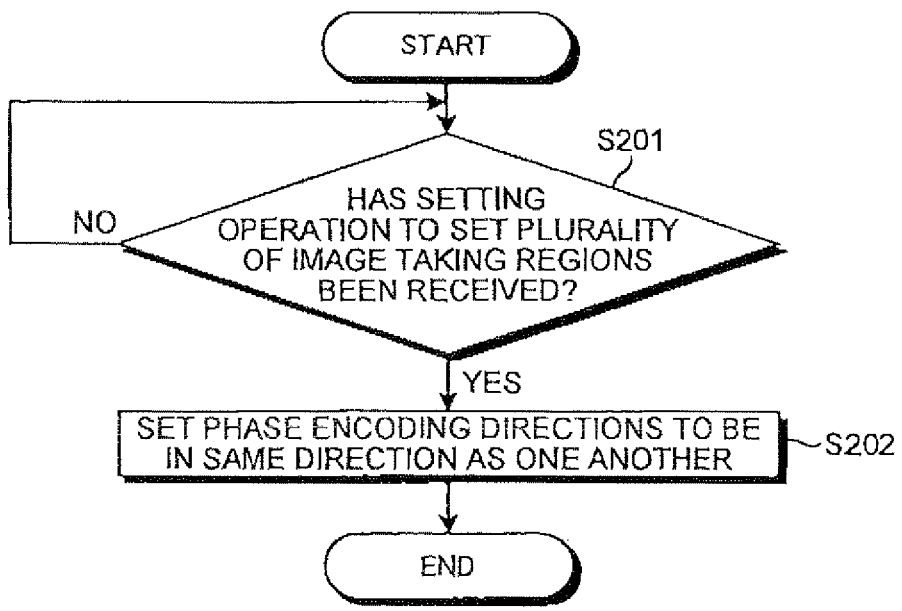
FIG. 6 is a flowchart for explaining a process performed by an MRI apparatus according to a modification example of the first embodiment.

In the following sections, a flow in a process according to the modification example of the first embodiment described above will be explained with reference to FIG. 6. FIG. 6 is a flowchart for explaining a process performed by an MRI apparatus according to the modification example of the first embodiment.

As shown in FIG. 6, the MRI apparatus 100 according to the modification example of the first embodiment judges whether the input unit 24 has received a setting operation to set a plurality of image taking regions within a position determining image, from the operator (step S201). In this situation, in the case where a setting operation to set a plurality of image taking regions has not been received (step S201: No), the MRI apparatus 100 goes into a stand-by state. On the contrary, in the case where a setting operation to set a plurality of image taking regions has been received (step S201: Yes), the direction setting unit 26b sets the phase encoding directions for the plurality of image taking regions to be in the same direction as one another (step S202), and the process is ended.

As a result of the process described above also, it is possible to reduce artifacts the MRI images that are caused by the phase encoding direction setting process.

Figure 7A:
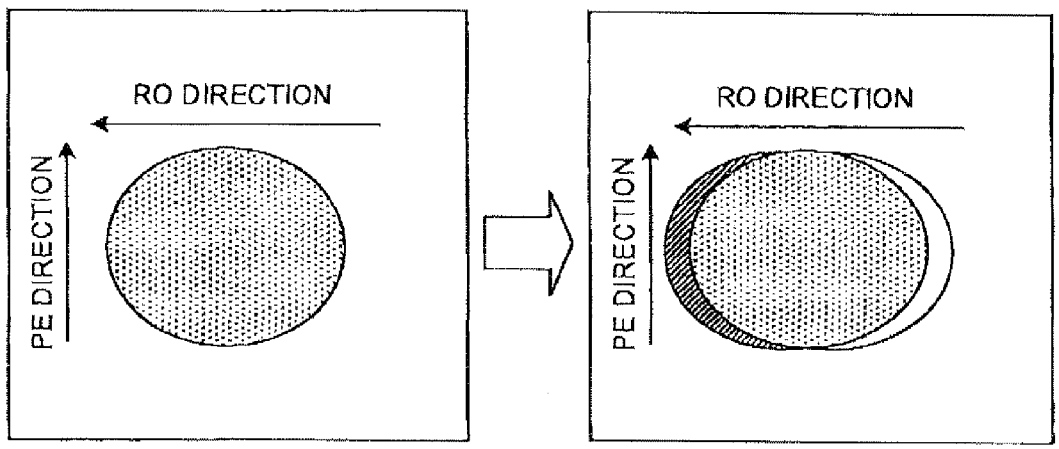
FIGS. 7A, 7B, and 7C are drawings for explaining advantageous effects of the first embodiment.
Figure 7B:
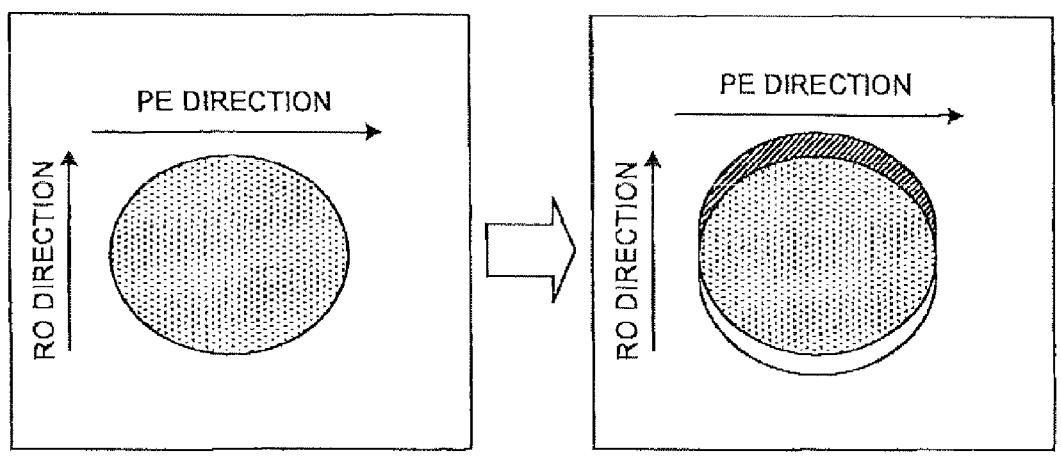
Figure 7C:
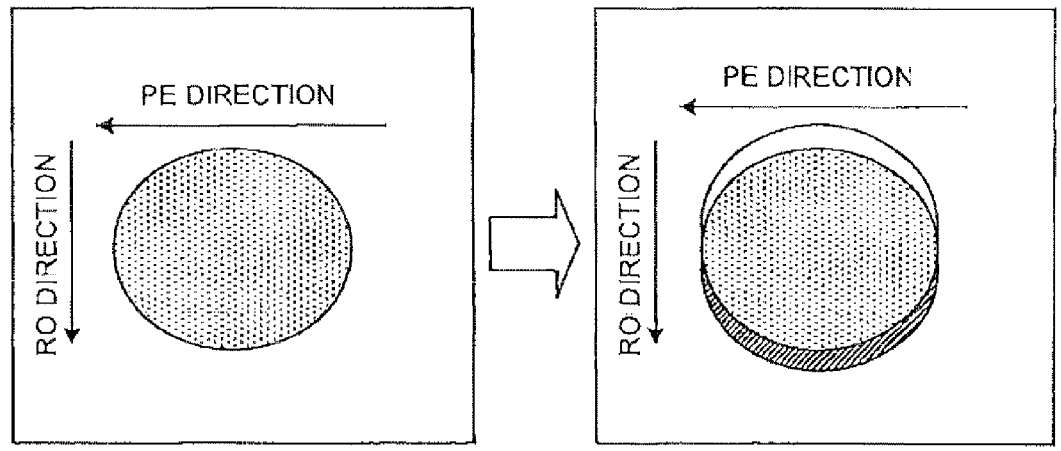

As a result of the process explained above with reference to FIGS. 5 and 6, it is possible to reduce aliasing artifacts and flow artifacts that are caused by the phase encoding direction setting process. Also, as a result of the process explained above with reference to FIGS. 5 and 6, it is possible to reduce the burden on the operator caused by the operation to set the plurality of image taking regions that is performed while chemical shift artifacts are taken into consideration. FIGS. 7A, 7B, and 7C are drawings for explaining advantageous effects of the first embodiment.

Chemical shift artifacts are artifacts that appear in MRI images due to a difference between the resonance frequency of fat and the resonance frequency of water. There is a difference (i.e., a chemical shift) of approximately "3.5 parts per million (ppm)" between the resonance frequency of fat and the resonance frequency of water. In MRI images, the impact of such a chemical shift appears in the read-out direction (hereinafter, the "RO direction"). More specifically, in MRI images, the region in which water and fat are both present is rendered as having shifted in the forward and the rearward directions of the RO direction. Even more specifically, the region that has shifted in the forward direction of the RO direction is darker, whereas the region that has shifted in the rearward direction of the RO direction is brighter.

For example, let us discuss a situation in which the RO direction has been set from the right toward the left, whereas the phase encoding direction (hereinafter, the "PE direction") has been set from the bottom toward the top, as shown in the left portion of FIG. 7A. In that situation, as shown in the right portion of FIG. 7A, the region resulting from the image taking target having shifted toward the left-hand side is rendered darker, whereas the region resulting from the image taking target having shifted toward the right-hand side is rendered brighter.

As another example, let us discuss a situation in which the RO direction has been set from the bottom toward the top, whereas the PE direction has been set from the left toward the right, as shown in the left portion of FIG. 7B. In that situation, as shown in the right portion of FIG. 7B, the region resulting from the image taking target having shifted toward the top is rendered darker, whereas the region resulting from the image taking target having shifted toward the bottom is rendered brighter.

As yet another example, let us discuss a situation in which the RO direction has been set from the top toward the bottom, whereas the PE direction has been set from the right toward the left, as shown in the left portion of FIG. 7C. In that situation, as shown in the right portion of FIG. 7C, the region resulting from the image taking target having shifted toward the bottom is rendered darker, whereas the region resulting from the image taking target having shifted toward the top is rendered brighter.

For example, to measure the size in the radial direction of an affected site of an examined subject rendered in an MRI image, the operator sets the RO direction and the PE direction while taking the chemical shift artifacts described above into consideration. In other words, to measure the size in the up-and-down radial direction of the affected site, the operator sets the PE direction for the image taking region to be in the up-and-down direction so that chemical shift artifacts do not occur in the up-and-down direction. For example, the operator sets the PE direction as shown in the left portion of FIG. 7A. It should be noted, however, that the direction of the RO direction is determined by the direction of the PE direction. Accordingly, in the case where a plurality of image taking regions have been set, if the directions of the PE directions are different from one another, the directions of the RO directions are also different from one another. In that situation, the MRI image includes both an image taking region in which the right-hand side of the affected site is brighter and an image taking region in which the left-hand side of the affected site is brighter. For example, when the operator wishes to measure the size of the affected site as well as to make a detailed observation of the right-hand side of the affected site, it is not desirable to have a situation in which the chemical shift artifact appearing pattern is different for each of the image taking regions.

As another example, to measure the size in the left-and-right radial direction of an affected site, the operator sets the PE direction for the image taking region to be in the left-and-right direction so that chemical shift artifacts do not occur in the left-and-right direction. For example, the operator sets the PE direction to be in a direction from the left toward the right, as shown in the left portion of FIG. 7B. However, in the case where a plurality of image taking regions are set, there is a possibility that the PE direction may be set to be in a direction from the right toward the left, as shown in the left portion of FIG. 7C, depending on how setting operations are performed by the operator. As explained above, the direction of the RO direction is determined by the direction of the PE direction. Accordingly, there is a possibility that the MRI image may include both an image taking region in which the bottom side of the affected site is brighter (see the right portion of FIG. 7B) and an image taking region in which the top side of the affected site is brighter (see the right portion of FIG. 7C). For example, when the operator wishes to measure the size of the affected site as well as to make a detailed observation of the bottom side of the affected site, it is not desirable to have a situation in which the chemical shift artifact appearing pattern is different for each of the image taking regions.

To cope with these situations, when the direction setting unit 26b performs the process to collectively set the PE directions as described above, it is possible to reduce the burden on the operator caused by the PE direction setting process that is performed while the chemical shift artifacts are taken into consideration.

Figure 8:
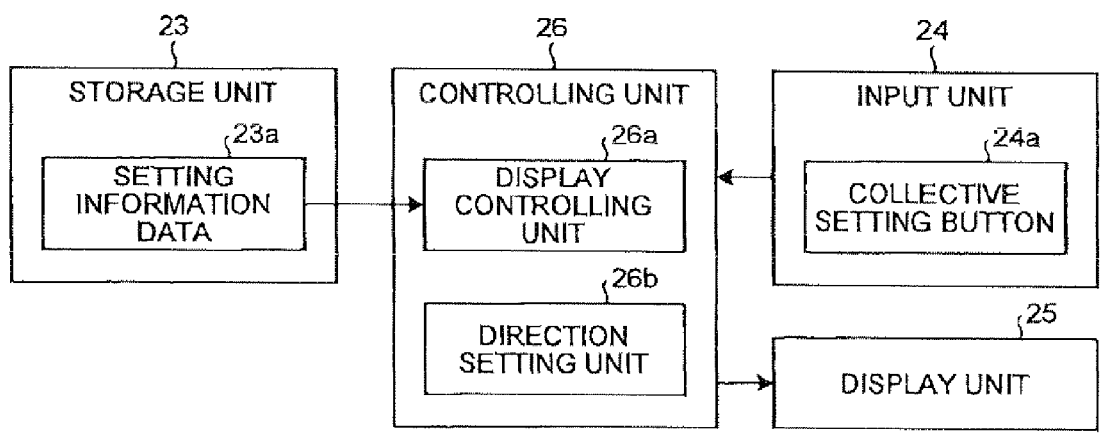
FIG. 8 is a drawing for explaining configurations of a controlling unit and a storage unit according to a second embodiment.
Figure 11:
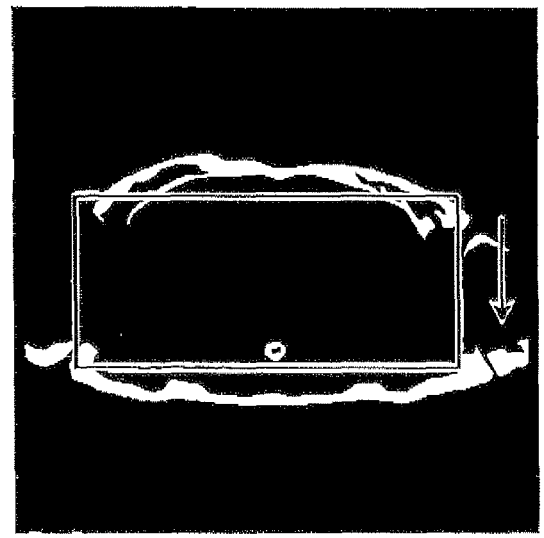

As a second embodiment, an example in which the phase encoding direction to be achieved in the collective setting operation is determined in advance according to image taking conditions of an MRI image will be explained, with reference to FIGS. 8, 9A, 9B, 10, and 11. FIG. 8 is a drawing for explaining configurations of a controlling unit and a storage unit according to the second embodiment. FIGS. 9A and 9B are drawings for explaining setting information data. FIGS. 10 and 11 are drawings for explaining a direction setting unit according to the second embodiment.

As shown in FIG. 8, the MRI apparatus 100 according to the second embodiment is different from the MRI apparatus according to the first embodiment in that the storage unit 23 stores therein setting information data 23a, and also, the process performed by the direction setting unit 26b according to the second embodiment is performed based on the setting information data 23a. In the following sections, the second embodiment will be explained while a focus is placed on these differences.

The input unit 24 shown in FIG. 8 receives, from the operator, a setting operation to set "information that is related to the image taking process" including an image taking region within a position determining image and image taking conditions for an MRI image to be taken in the image taking region. Further, based on the "information that is related to the image taking process" and that has been received by the input unit 24, the direction setting unit 26b according to the second embodiment sets a phase encoding direction for the image taking region. More specifically, the direction setting unit 26b according to the second embodiment obtains the phase encoding direction corresponding to the "information that is related to the image taking process" out of the setting information data 23a. Accordingly, the direction setting unit 26b according to the second embodiment sets the phase encoding direction for the image taking region. The setting information data 23a is data that has been stored in the storage unit 23 in advance by the operator of the MRI apparatus 100. For example, the setting information data 23a may be setting information in which information regarding the image taking site, the image taking cross-section direction, and the body position of the examined subject P is kept in correspondence with the phase encoding direction.

For example, as shown in FIG. 9A, the setting information data 23a stores therein data indicating "image taking site: spine", "image taking cross section: axial", and "phase encoding direction: front-to-back direction". As another example, as shown in FIG. 9A, the setting information data 23a stores therein data indicating "image taking site: spine", "image taking cross section: sagittal", and "phase encoding direction: head-to-toe direction". It should be noted, however, that it is not possible to set the "front-to-back direction" or the "head-to-toe direction" as a single direction with respect to the coordinate system that has been set with the MRI apparatus 100. For example, the "front-to-back direction" in the coordinate system that has been set with the MRI apparatus 100 varies depending on whether the examined subject P is in a supine position or in a prone position. For this reason, in one of the examples shown in FIG. 9A, information indicating "phase encoding direction: front-to-back direction" is kept in correspondence with the information indicating "image taking site: spine", "image taking cross section: axial", and "body position: supine", while being identified as "direction 11". Similarly, in another one of the examples shown in FIG. 9A, the information indicating "phase encoding direction: front-to-back direction" is kept in correspondence with the information indicating "body position: prone", while being identified as "direction 12". Further, in yet another one of the examples shown in FIG. 9A, the information indicating "phase encoding direction: front-to-back direction" is kept in correspondence with the information indicating "body position: lying on his/her side (right arm)", while being identified as "direction 13". Furthermore, in yet another one of the examples shown in FIG. 9A, the information indicating "phase encoding direction: front-to-back direction" is kept in correspondence with the information indicating "body position: lying on his/her side (left arm)", while being identified as "direction 14".

Further, in yet another one of the examples shown in FIG. 9A, the information indicating "phase encoding direction: head-to-toe direction" is kept in correspondence with the information indicating "image taking site: spine", "image taking cross section: sagittal", and "body position: supine", while being identified as "direction 21". Similarly, in yet another one of the examples shown in FIG. 9A, the information indicating "phase encoding direction: head-to-toe direction" is kept in correspondence with the information indicating "body position: prone", while being identified as "direction 22". Further, in yet another one of the examples shown in FIG. 9A, the information indicating "phase encoding direction: head-to-toe direction" is kept in correspondence with the information indicating "body position: lying on his/her side (right arm)", while being identified as "direction 23". Furthermore, in yet another one of the examples shown in FIG. 9A, the information indicating "phase encoding direction: head-to-toe direction" is kept in correspondence with the information indicating "body position: lying on his/her side (left arm)", while being identified as "direction 24".

In this situation, before the position determining image is taken, the operator has input an image taking plan for the MRI image in advance. The image taking plan contains the "information that is related to the image taking process". In other words, the image taking plan contains, as image taking conditions to be used during a main image taking process, information indicating the image taking site, the image taking cross section, and the body position of the examined subject for the MRI image. The direction setting unit 26b according to the second embodiment sets the phase encoding direction for the image taking region based on the setting information data 23a. More specifically, in the case where the operator has set one or more image taking regions within the position determining image and subsequently has pressed the collective setting button 24a, the direction setting unit 26b obtains the information indicating the image taking site, the image taking cross section, and the body position for the MRI image corresponding to the main image taking process out of the image taking plan. For example, the direction setting unit 26b obtains information indicating "image taking site: spine", "image taking cross section: axial", and "body position: supine". An arrangement is acceptable in which the direction setting unit 26b obtains the information indicating the image taking site based on information related to the type of the RF coil (i.e., the reception coil 8) used for the image taking process (e.g., information indicating that the RF coil is an RF coil used for the spine).

Further, the direction setting unit 26b obtains the information indicating "phase encoding direction: front-to-back direction (i.e., direction 11)" that is kept in correspondence with the obtained information indicating "image taking site: spine", "image taking cross section: axial", and "body position: supine", out of the setting information data 23a.

After that, as shown in FIG. 10 for example, the direction setting unit 26b sets the phase encoding directions for the image taking regions to be in the front-to-back direction (i.e., direction 11).

As explained above, the direction setting unit 26b sets the phase encoding direction for the image taking region, based on the information that indicates the image taking site, the image taking cross-section direction, and the body position of the examined subject P and that has been received by the input unit 24 as the image taking conditions.

Further, the setting information data 23a may be information shown in FIG. 9B as an example. For example, the setting information data 23a may store therein data indicating "shape of image taking site: rectangle" and "phase encoding direction: short side".

Further, in the case where the operator has set one or more image taking regions within the position determining image and subsequently has pressed the collective setting button 24a, the direction setting unit 26b obtains information indicating the shape of the image taking region serving as the "information that is related to the image taking process". After that, in the case there the shape of the image taking region that has been set by the operator is a rectangle, the direction setting unit 26b sets the short side of the image taking region as the phase encoding direction. For example, as shown in FIG. 11, in the case where a rectangle image taking region has been set for the purpose of obtaining an MRI image in the main image taking process on an axial cross section, the direction setting unit 26b sets the phase encoding direction to be the short side of the rectangle, based on the setting information data 23a. As a result, in the case where MRI images are taken in rectangle image taking regions on a plurality of axial cross sections, the phase encoding directions are set to be the short sides of the rectangles in a collective manner.

As explained above, in the case where the shape of the image taking region that has been received by the input unit 24 is a rectangle, the direction setting unit 26b sets the short side of the image taking region as the phase encoding direction.

It should be noted that, as shown in FIG. 11, because the image taking site is the "spine" and the image taking cross section is the "axial cross section", the direction setting unit 26b sets the short side corresponding to the front-to-back direction as the phase encoding direction.

Figure 12:
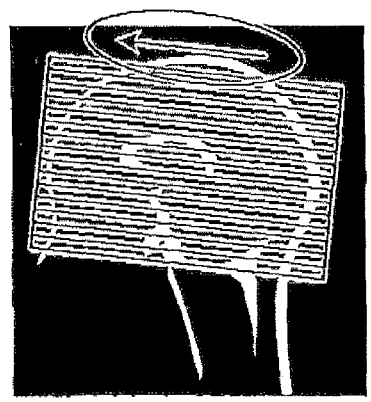
FIGS. 12, 13, and 14 are drawings for explaining other specific examples related to a phase encoding direction setting process that is performed by the direction setting unit according to the second embodiment while using the setting information data, besides the phase encoding direction setting processes that are illustrated in FIGS. 10 and 11.
Figure 13:
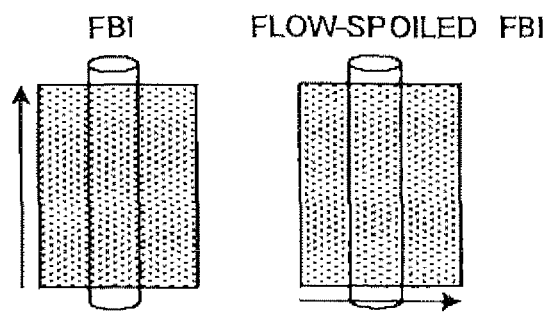
Figure 14:
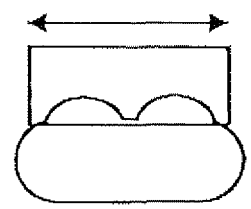

Further, besides the phase encoding direction setting process explained with reference to FIGS. 11 and 12, the direction setting unit 26b according to the second embodiment may perform phase encoding direction setting processes while using various setting information data, as explained below with reference to FIGS. 12 to 14. FIGS. 12, 13, and 14 are drawings for explaining other specific examples related to phase encoding direction setting processes that are performed by the direction setting unit according to the second embodiment while using the setting information data, besides the phase encoding direction setting process that is illustrated in FIGS. 10 and 11.

For example, the setting information data 23a stores therein data in which a phase encoding direction is kept in correspondence with information indicating the image taking site, the image taking cross-section direction, the type of the pulse sequence used for the image taking process, the image taking direction, and the body position of the examined subject P. In the example shown in FIG. 12, the setting information data 23a stores therein data in which information indicating "phase encoding direction: PA direction (direction 3)" is kept in correspondence with information indicating "image taking site: head", "image taking cross section: axial", "sequence: EPI", "image taking method: diffusion", and "body position: supine". The setting information data 23a shown in FIG. 12 indicates that, in the case where the image taking site is set to be the "head", the image taking cross-section direction is set to be the "axial cross-section direction", the type of the pulse sequence is set to be the "Echo Planar Imaging (EPI)", and the image taking method is set to be the "diffusion weighted image" taking method, the phase encoding direction that is kept in correspondence therewith is the PA direction, which is the direction from the posterior to the anterior. Also, the setting information data 23a shown in FIG. 12 indicates that, in the case where the "body position: supine" is true, the "phase encoding direction: PA direction" corresponds to "direction 3".

In this situation, let us discuss a situation in which the operator has set a plurality of image taking regions in an axial cross-section direction within a sagittal image obtained by taking the image of the head of an examined subject, for the purpose of observing a signal difference between the left brain and the right brain. In that situation, the operator sets, as image taking conditions, "image taking site: head" and "image taking cross section: axial". After that, let us assume that the operator has set EPI as the type of the pulse sequence, the diffusion weighted image taking method as the image taking method, and a supine position as the body position of the examined subject P.

In that situation, the direction setting unit 26b refers to the setting information data 23a and sets the phase encoding directions for the plurality of image taking regions to be in the PA direction (direction 3) in a collective manner, as shown in FIG. 12. In other words, the direction setting unit 26b sets the phase encoding direction for the image taking region, based on information that indicates an image taking site, an image taking cross-section direction, a body position of an examined subject, a type of a pulse sequence to be used for the image taking process and an image taking method and that has been received by the input unit 24 as the image taking condition.

Alternatively, the setting information data 23a stores therein data in which a phase encoding direction is kept in correspondence with the type of the pulse sequence used for the image taking process. In recent years, methods for taking an MRI image in which bloodstreams are rendered clearly without the use of a contrast agent have been developed. A Fresh Blood Imaging (FBI) sequence and a Flow-Spoiled FBI sequence are known as pulse sequences that can be used in such an image taking process. FBI is an imaging taking method to repeat every set of a plurality of heart beats an operation of collecting echo signals of a certain slice encode by using cardiac synchronization or pulse wave synchronization. TR (Repetition Time) and TE (Echo Time) in FBI are set within the range where the T2 weighted image can be acquired. By matching the phase encoding direction to the direction in which the blood vessel runs, the fluid can be emphasized because signals that spread by the effect of blur overlap over the number of pixels, and the effect of flow void along to the phase encoding direction can be decreased. So, in FBI, by setting the phase encoding direction so as to extend parallel to the direction in which the blood vessel runs, an image in which the fluid such as blood, cerebrospinal fluid, or the like is emphasized can be obtained. Moreover, in diastole phase, both signal strength of artery and vein is high because both flow velocity of artery and vein is slow. So, in diastole phase, an image in which both of artery and vein is emphasized can be obtained. In contrast, in systolic phase, signal strength of artery falls because the change of blood velocity in vein is few and the change of blood velocity in artery quickens up. So, in systolic phase, an image in which only artery is emphasized can be obtained. So, in FBI, an image in which only artery is emphasized can be obtained by subtracting the image of systolic phase from the image of diastole phase after image taking in diastole phase and systolic phase, respectively. However, in FBI, although the artery of a large blood vessel and the vein of a large blood vessel can be separated, the signal suppression of an artery in systolic phase becomes insufficient in the blood vessel with a slow flow such as the peripheral vessels. As a result, in FBI, the artery of the blood vessel with a slow flow such as the peripheral vessels might not be emphasized in the subtracted image. Here, the effect of flow-dephasing by magnetic gradient field of read-out (RO) is achieved by setting the RO direction in the direction in which the blood vessel runs. As a result, the artery signal is suppressed. In Flow-Spoiled FBI, when signals are collected, a spoiler magnetic gradient field pulse which applies the difference of magnetic gradient field strength along to the RO direction according to the space position is added. As a result, the phase of the artery signal is distributed and the artery signal is suppressed. Therefore, in Flow-Spoiled FBI, the phase encoding direction is set so as to extend orthogonal to the direction in which the blood vessel runs. When an image taking process is performed by using the FBI sequence that is a pulse sequence to perform FBI or the Flow-Spoiled FBI sequence that is a pulse sequence to perform Flow-Spoiled FBI, the image taking region is set so that, according to either one of the methods, the blood vessels are included therein and so that the blood vessels are included in a large area along the bloodstream direction. However, as described above, when the FBI sequence is used, the phase encoding direction needs to be set so as to extend parallel to the direction in which the blood vessel runs, as shown in the left portion of FIG. 13.

Also, as described above, when the Flow-Spoiled FBI sequence is used, the phase encoding direction needs to be set so as to extend orthogonal to the direction in which the blood vessel runs, as shown in the right portion of FIG. 13.

For this reason, the setting information data 23a stores therein data indicating that, when the FBI sequence has been set as an image taking condition, the phase encoding direction should be set so as to extend "parallel to the direction in which the blood vessel runs". Further, the setting information data 23a stores therein data indicating that, when the Flow-Spoiled FBI sequence has been set as an image taking condition, the phase encoding direction should be set so as to extend "orthogonal to the direction in which the blood vessel runs". With this arrangement, the direction setting unit 26b refers to the setting information data 23a and sets the phase encoding direction for the image taking region to be in the direction shown in the left portion of the FIG. 13 or to be in the direction shown in the right portion of FIG. 13. In other words, the direction setting unit 26b sets the phase encoding direction for the image taking region, based on information that indicates an image taking site and a type of a pulse sequence to be used for the image taking process and that has been received by the input unit 24 as the image taking condition.

Alternatively, the setting information data 23a stores therein data in which a phase encoding direction is kept in correspondence with the type of the reception coil 8 to be used for the image taking process. When an image of the chest of an examined subject is to be taken, it is desirable if, generally speaking, the phase encoding direction is in a front-to-back direction. In contrast, when an image of the breast is to be taken while an image taking region on an axial cross section is set, it is desirable to set the phase encoding direction to be in the left-and-right direction of the image taking region, for the purpose of avoiding occurrence of aliasing artifacts. For this reason, the setting information data 23a stores therein data indicating that, in the case where "coil: breast" and "image taking cross section: axial" have been set as image taking conditions, the phase encoding direction should be in the "left-and-right" direction, as shown in FIG. 14. It should be noted that, when a "breast coil", which is the reception coil 8 exclusively used for taking an image of the breast, has been set for the purpose of taking an MRI image of the breast, the body position of the examined subject P should normally be a prone position.

With this arrangement, the direction setting unit 26b refers to the setting information data 23a and sets the phase encoding direction for the image taking region to be in the left-and-right direction, as shown in FIG. 14. In other words, the direction setting unit 26b sets the phase encoding direction for the image taking region, based on information that indicates an image taking site, an image taking cross-section direction and a type of a reception coil to be used for the image taking process and that has been received by the input unit 24 as the image taking condition.

In this way, the direction setting unit 26b sets the phase encoding direction for the image taking region, based on information that indicates at least two combinations of the following and that has been received by the input unit 24 as the image taking condition: an image taking site; an image taking cross-section direction; a body position of an examined subject; a type of a pulse sequence to be used for the image taking process; an image taking method; and a type of a reception coil to be used for the image taking process. Alternatively, the direction setting unit 26b may set the phase encoding direction for the image taking region, based on information that indicates at least one of the following and that has been received by the input unit as the image taking condition: an image taking site; an image taking cross-section direction; a body position of an examined subject; a type of a pulse sequence to be used for the image taking process; an image taking method; and a type of a reception coil to be used for the image taking process. For example, the direction setting unit 26b may set the phase encoding direction for the image taking region, based on information that indicates a type of a pulse sequence to be used for the image taking process and that has been received by the input unit 24 as the image taking condition.

Like in the first embodiment, the display controlling unit 26a shown in FIG. 8 exercises control so that the display unit 25 displays the phase encoding direction for the image taking region that has been set by the direction setting unit 26b.

Figure 15:
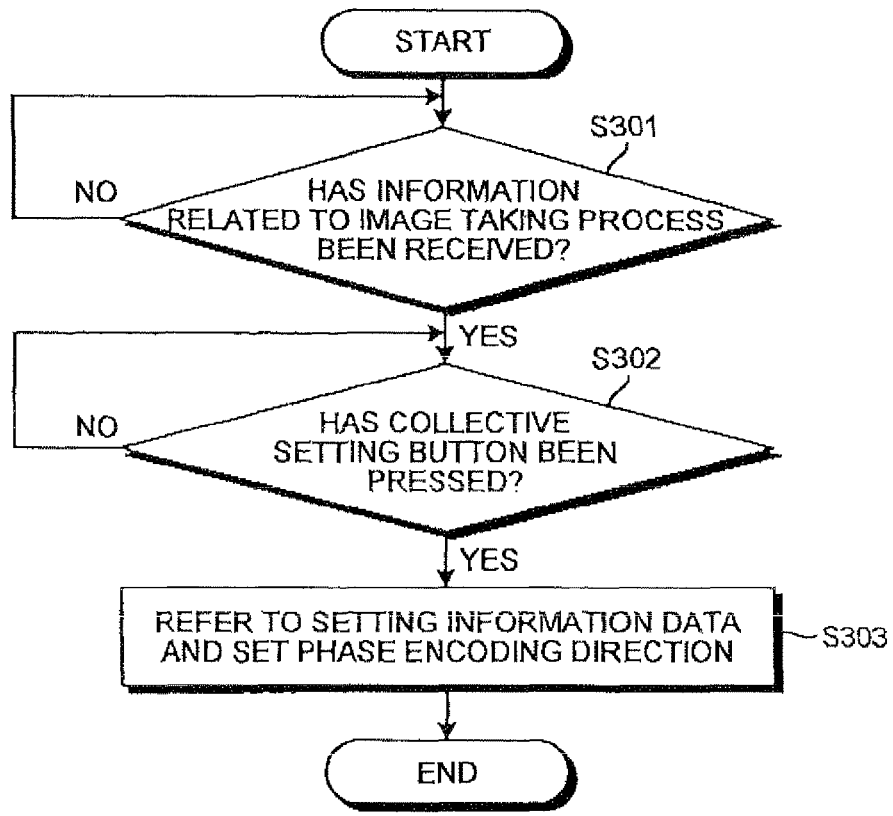
FIG. 15 is a flowchart for explaining a process performed by an MRI apparatus according to the second embodiment.

Next, a process performed by the MRI apparatus 100 according to the second embodiment will be explained, with reference to FIG. 15. FIG. 15 is a flowchart for explaining the process performed by the MRI apparatus according to the second embodiment.

As shown in FIG. 15, the MRI apparatus 100 according to the second embodiment judges whether the input unit 24 has received information that is related to the image taking process within a position determining image (step S301). In this situation, in the case where the information that is related to the image taking process has not been received (step S301: No), the MRI apparatus 100 goes into a stand-by state. On the contrary, in the case where the information that is related to the image taking Process has been received (step S301: Yes), the MRI apparatus 100 judges whether the collective setting button 24a has been pressed by the operator (step S302).

In this situation, in the case where the collective setting button 24a has not been pressed by the operator (step S302: No), the MRI apparatus 100 goes into a stand-by state.

On the contrary, in the case where the collective setting button 24a has been pressed by the operator (step S302: Yes), the direction setting unit 26b refers to the setting information data 23a and sets a phase encoding direction for the image taking region (step S303), and the process is ended.

As explained above, according to the second embodiment, the input unit 24 receives, from the operator, the setting operation to set the information that is related to the image taking process and that includes the image taking region within the position determining image and the image taking conditions for the magnetic resonance image to be taken in the image taking region. Based on the information that is related to the image taking process and that has been received by the input unit 24, the direction setting unit 26b sets the phase encoding direction for the image taking region. For example, based on the information that indicates the image taking site the age taking cross-section direction, and the body position of the examined subject P and that has been received by the input unit 24 as the image taking conditions, the direction setting unit 26b sets the phase encoding direction for the image taking region. As another example, based on the information that indicates at least one of the following and that has been received by the input unit 24 as the image taking conditions, the direction setting unit 26b sets the phase encoding direction for the image taking region: the image taking site; the image taking cross-section direction; the body position of the examined subject; the type of the pulse sequence to be used for the image taking process; the image taking method; and the type of the reception coil to be used for the image taking process.

As a result, according to the second embodiment, it is possible to set the phase encoding direction for the image taking region, in a collective manner, to be in the phase encoding direction desired by the operator in accordance with the image taking conditions. Thus, it is possible to make it easy to set the phase encoding direction for the image taking region.

Further, according to the second embodiment, in the case where the shape of the image taking region that has been received by the input unit 24 is a rectangle, the direction setting unit 26b sets the short side of the image taking region as the phase encoding direction. Thus, it is possible to avoid the situation where a phase error in an MRI image is enlarged by a phase encoding direction that has been set to the long side of the rectangle. Consequently, it is possible to improve the image quality of the MRI image.

In the description of the second embodiment, the example has been explained in which the process by the direction setting unit 26b is performed based on the setting information data 23a, in the case where the collective setting button 24a has been pressed; however, the second embodiment is not limited to this example. More specifically, the second embodiment may be applied to a situation in which the direction setting unit 26b automatically sets the phase encoding direction in a collective manner based on the setting information data 23a, without receiving any phase encoding direction setting request from the operator.

Figure 16:
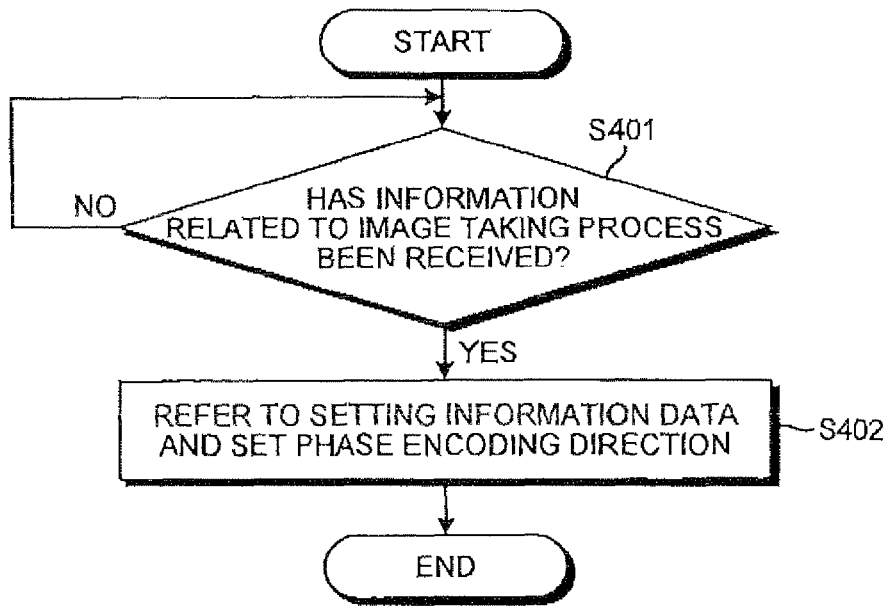
FIG. 16 is a flowchart for explaining a process performed by an MRI apparatus according to a modification example of the second embodiment.
Figure 17:
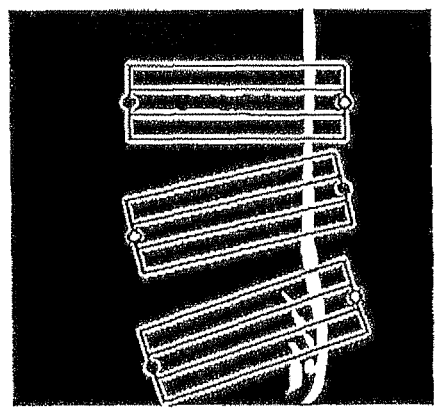
FIG. 17 is a drawing for explaining a conventional slab setting process.
Figure 18:
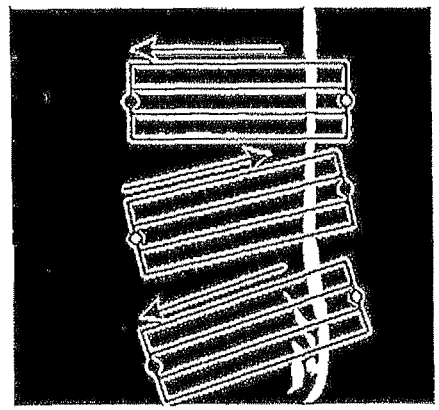
FIG. 18 is a drawing for explaining a problem in a conventional technique.

In the following sections, a flow in a process according to the modification example of the second embodiment described above will be explained, with reference to FIG. 16. FIG. 16 is a flowchart for explaining a process performed by an MRI apparatus according to the modification example of the second embodiment.

As shown in FIG. 16, the MRI apparatus 100 according to the modification example of the second embodiment judges whether the input unit 24 has received information that is related to the image taking process within a position determining image (step S401). In this situation, in the case where the information that is related to the image taking process has not been received (step S401: No), the MRI apparatus 100 goes into a stand-by state.

On the contrary, in the case where the information that is related to the image taking process has been received (step S401: Yes), the direction setting unit 26b refers to the setting information data 23a and sets the phase encoding direction for the image taking region (step S402), and the process is ended.

As a result of the process described above also, it is possible to make it easy to set the phase encoding direction for the image taking region.

As explained above, according to the first and the second embodiments, it is possible to make it easy to set the phase encoding directions for a plurality of image taking regions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
an input unit that receives a setting operation to set a plurality of image taking regions within a position determining image, from an operator; and
a direction setting unit that sets phase encoding directions for the plurality of image taking regions to be in a same direction as one another, regardless of setting operations performed by the operator via the input unit.

2. The magnetic resonance imaging apparatus according to claim 1, wherein, in a case where a phase encoding direction setting request has been received from the operator via the input unit, the direction setting sets the phase encoding directions for the plurality of image taking regions to be in the same direction as one another.

3. The magnetic resonance imaging apparatus according to claim 1, further comprising: a display controlling unit that exercises control so as to cause a display unit to display the phase encoding directions for the plurality of image taking regions that have been set by the direction setting unit.

4. The magnetic resonance imaging apparatus according to claim 2, further comprising: a display controlling unit that exercises control so as to cause a display unit to display the phase encoding directions for the plurality of image taking regions that have been set by the direction setting unit.

5. A magnetic resonance imaging apparatus comprising:
   an input unit that receives, from an operator, a setting operation to set information that is related to an image taking process and that includes an image taking region within a position determining image and an image taking condition for a magnetic resonance image to be taken in the image taking region; and
   a direction setting unit that, based on the information that is related to the image taking process and that has been received by the input unit, sets a phase encoding direction for the image taking region.

6. The magnetic resonance imaging apparatus according to claim 5, wherein, in a case where a phase encoding direction setting request has been received from the operator via the input unit, the direction setting unit sets the phase encoding direction for the image taking region.

7. The magnetic resonance imaging apparatus according to claim 5, further comprising: a display controlling unit that exercises control so as to cause a display unit to display the phase encoding direction for the image taking region that has been set by the direction setting unit.

8. The magnetic resonance imaging apparatus according to claim 5, further comprising: a display controlling unit that exercises control so as to cause a display unit to display the phase encoding direction for the image taking region that has been set by the direction setting unit.

9. The magnetic resonance imaging apparatus according to claim 5, wherein the direction setting unit sets the phase encoding direction for the image taking region, based on information that indicates an image taking site, an image taking cross-section direction, and a body position of an examined subject and that has been received by the input unit as the image taking condition.

10. The magnetic resonance imaging apparatus according to claim 5, wherein, in a case where a shape of the image taking region that has been received by the input unit is a rectangle, the direction setting unit sets a short side of the image taking region as the phase encoding direction.

11. The magnetic resonance imaging apparatus according to claim 5, wherein the direction setting unit sets the phase encoding direction for the image taking region, based on information that indicates at least one of the following and that has been received by the input unit as the image taking condition: an image taking site; an image taking cross-section direction; a body position of an examined subject; a type of a pulse sequence to be used for the image taking process; an image taking method; and a type of a reception coil to be used for the image taking process.

12. The magnetic resonance imaging apparatus according to claim 11, wherein the direction setting unit sets the phase encoding direction for the image taking region, based on information that indicates at least two combinations of the following and that has been received by the input unit as the image taking condition: an image taking site; an image taking cross-section direction; a body position of an examined subject; a type of a pulse sequence to be used for the image taking process; azo image taking method; and a type of a reception coil to be used for the image taking process.

13. The magnetic resonance imaging apparatus according to claim 12, wherein the direction setting unit sets the phase encoding direction for the image taking region, based on information that indicates an image taking site, an image taking cross-section direction, a body position of an examined subject, a type of a pulse sequence to be used for the image taking process and an image taking method and that has been received by the input unit as the image taking condition.

14. The magnetic resonance imaging apparatus according to claim 12, wherein the direction setting unit sets the phase encoding direction for the image taking region, based on information that indicates an image taking site and a type of a pulse sequence to be used for the image taking process and that has been received by the input unit as the image taking condition.

15. The magnetic resonance imaging apparatus according to claim 12, wherein the direction setting unit sets the phase encoding direction for the image taking region, based on information that indicates an image taking site, an image taking cross-section direction and a type of a reception coil to be used for the image taking process and that has been received by the input unit as the image taking condition.

16. A magnetic resonance imaging method comprising:
   a process performed by an input unit to receive a setting operation to set a plurality of image taking regions within a position determining image, from an operator; and
   a process performed by a direction setting unit to set phase encoding directions for the plurality of image taking regions to be in a same direction as one another, regardless of setting operations performed by the operator via the input unit.

17. A magnetic resonance imaging method comprising:
   a process performed by an input unit to receive, from an operator, a setting operation to set information that is related to an image taking process and that includes an image taking region within a position determining image and an image taking condition for a magnetic resonance image to be taken in the image taking region; and
   a process performed by a direction setting unit to, based on the information that is related to the image taking process and that has been received by the input unit, set a phase encoding direction for the image taking region.

* * * * *